US00PP28354P3

(12) United States Plant Patent
Bullis

(10) Patent No.: US PP28,354 P3
(45) Date of Patent: Aug. 29, 2017

(54) ***AECHMEA* PLANT NAMED 'PATRICIA'S SECRET'**

(50) Latin Name: ***Aechmea eurycorymbus*×(*Aechmea chantinii*×*Aechmea tessmannii*)**
Varietal Denomination: Patricia's Secret

(71) Applicant: Patricia Gomez Bullis, Princeton, FL (US)

(72) Inventor: Patricia Gomez Bullis, Princeton, FL (US)

(73) Assignee: Bullis Bromeliads, Princeton, FL (US)

( * ) Notice: Subject to any disclaimer, the term of this patent is extended or adjusted under 35 U.S.C. 154(b) by 6 days.

(21) Appl. No.: 14/545,632

(22) Filed: May 29, 2015

(65) Prior Publication Data

US 2016/0353633 P1 Dec. 1, 2016

(51) Int. Cl.
*A01H 5/02* (2006.01)

(52) U.S. Cl.
USPC ..... Plt./370

(58) Field of Classification Search
USPC ..... Plt./370
See application file for complete search history.

(56) References Cited

PUBLICATIONS

BromeliAdvisory Mar. 2014, retrieved on Sep. 19, 2016, retrieved from the Internet at <http://www.bssf-miami.org/newsbulletins/2014-03_full.pdf> pp. 1-9.*

Flckr 36th Annual Show and Sale Bromeliad Society of South Florida Miami, Florida Mar. 1-2, 2014 Entry 99, retrieved on Sep. 19, 2016, retrieved from the Internet at <http://www.bssf-miami.org/newsbulletins/2014-03_full.pdf> 3 pp.*

* cited by examiner

*Primary Examiner* — June Hwu
(74) *Attorney, Agent, or Firm* — C. A. Whealy

(57) ABSTRACT

A new and distinct cultivar of *Aechmea* plant named 'Patricia's Secret', characterized by its upright and outwardly arching growth habit; unique yellow green and green variegated leaves with green-colored margins and yellow green-colored longitudinal stripes with a rosy pink-colored blush; inflorescences held upright and above the foliar plane on strong orange-colored scapes; tightly branched inflorescences with greyed orange-colored flower bracts with greyed yellow-colored sepals; and long-lasting inflorescences.

1 Drawing Sheet

Botanical designation: *Aechmea eurycorymbus*×(*Aechmea chantinii*×*Aechmea tessmannii*).

Cultivar denomination: 'PATRICIA'S SECRET'.

BACKGROUND OF THE INVENTION

The present invention relates to a new and distinct *Aechmea* plant, botanically known as *Aechmea eurycorymbus*×(*Aechmea chantinii*×*Aechmea tessmannii*) and hereinafter referred to by the cultivar name 'Patricia's Secret'.

The new *Aechmea* plant is a naturally-occurring whole plant mutation of the *Aechmea eurycorymbus*×(*Aechmea chantinii*×*Aechmea tessmannii*) 'Patricia', not patented. The new *Aechmea* plant was discovered and selected by the Inventor from within a population of plants of 'Patricia' in a controlled greenhouse environment in Princeton, Fla. in 2008.

Asexual reproduction of the new *Aechmea* plant by offsets in a controlled greenhouse environment in Princeton, Fla. since 2008 has shown that the unique features of this new *Aechmea* plant are stable and reproduced true to type in successive generations.

SUMMARY OF THE INVENTION

Plants of the new *Aechmea* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Patricia's Secret'. These characteristics in combination distinguish 'Patricia's Secret' as a new and distinct *Aechmea* plant:

1. Upright and outwardly arching growth habit.
2. Unique yellow green and green variegated leaves with green-colored margins and yellow green-colored longitudinal stripes with a rosy pink-colored blush.
3. Inflorescences held upright and above the foliar plane on strong orange-colored scapes.
4. Tightly branched inflorescences with greyed orange-colored flower bracts with greyed yellow-colored sepals.
5. Long-lasting inflorescences. p Plants of the new *Aechmea* differ from plants of the parent, 'Patricia', primarily in leaf color as plants of 'Patricia' have solid green-colored leaves with a bronze-colored blush.

Plants of the new *Aechmea* can be compared to plants of *Aechmea chantinii* 'Samurai', not patented. Plants of the new *Aechmea* and 'Samurai' differ primarily in the following characteristics:

1. Plants of the new *Aechmea* are taller than plants of 'Samurai'.

2. Leaves of plants of the new *Aechmea* are broader than leaves of plants of 'Samurai'.
3. Variegation of leaves of plants of the new *Aechmea* is more stable than variegation of leaves of 'Samurai'.
4. Plants of the new *Aechmea* have longer-lasting inflorescences than plants of 'Samurai'.

BRIEF DESCRIPTION OF THE PHOTOGRAPHS

The accompanying colored photographs illustrate the overall appearance of the new *Aechmea* plant showing the colors as true as it is reasonably possible to obtain in colored reproductions of this type. Colors in the photographs may differ slightly from the color values cited in the detailed botanical description which accurately describe the colors of the new *Aechmea* plant.

The photograph on the right side of the sheet is a side perspective view of a typical flowering plant of 'Patricia's Secret' grown in a container.

The photograph on the left side of the sheet is a close-up view of a typical inflorescence of 'Patricia's Secret'.

DETAILED BOTANICAL DESCRIPTION

The aforementioned photographs and following observations, measurements and values describe plants grown in 20-cm containers during the winter and spring in a polypropylene-covered shadehouse in Princeton, Fla. During the production of the plants, day temperatures ranged from 28° to 30° C., night temperatures ranged from 18° C. to 22° C. and light levels ranged from 3,200 to 5,000 foot-candles. Plants were 14 months old when the photographs and description were taken. In the following description, color references are made to The Royal Horticultural Society Colour Chart, 2007 Edition, except where general terms of ordinary dictionary significance are used.

Botanical classification: *Aechmea eurycorymbus*×(*Aechmea chantinii*×*Aechmea tessmannii*) 'Patricia's Secret'.

Parentage: Naturally-occurring whole plant mutation of the *Aechmea eurycorymbus*×(*Aechmea chantinii*×*Aechmea tessmannii*) 'Patricia', not patented.

Propagation:

*Type*.—By offsets.

*Time to initiate roots, summer*.—About 30 to 45 days at temperatures ranging from 28° C. to 30° C.

*Time to initiate roots, winter*.—About 45 to 60 days at temperatures ranging from 28° C. to 30° C.

*Time to produce a rooted young plant, summer*.—About three months at temperatures ranging from 28° C. to 30° C.

*Time to produce a rooted young plant, winter*.—About six months at temperatures ranging from 18° C. to 22° C.

*Root description*.—Medium in thickness, fibrous; yellow and white in color, actual color will depend on substrate composition.

*Rooting habit*.—Moderately freely branching; medium density.

Plant description:

*Plant and growth habit*.—Upright and outwardly arching growth habit; rosette leaves are erect when young, becoming outwardly arching with development; plants readily produce offsets; vigorous growth habit.

*Plant height, soil surface to top of leaf canopy*.—About 74.3 cm.

*Plant height, soil surface to top of inflorescence*.—About 80 cm.

*Plant diameter or spread*.—About 90 cm.

Leaf description:

*Arrangement*.—Rosette, spiral phyllotaxis; leaves clasping; simple.

*Length*.—About 64.8 cm.

*Width*.—About 9.2 cm; at the base, about 15.5 cm.

*Shape*.—Lanceolate, strap-like.

*Apex*.—Cuspidate.

*Base*.—Truncate.

*Margin*.—Serrate and spinose.

*Aspect*.—Upright to arching with development.

*Texture, upper and lower surfaces*.—Smooth, glabrous; leathery; stiff.

*Luster, upper surface*.—Slightly glossy.

*Luster, lower surface*.—Matte.

*Venation*.—Parallel.

*Color*.—Developing leaves, upper surface: Towards the margins, 146B; central parallel longitudinal stripes, 146C to 146D, 147B and 160D. Developing leaves, lower surface: Towards the margins, 147C; central parallel longitudinal stripes, 146D, 147C and 160D. Fully expanded leaves, upper surface: Towards the margins, 146B; central parallel longitudinal stripes, 146C, 147A and 160D; overlain with close to 182B to 182C; venation, close to 146B. Fully expanded leaves, lower surface: Towards the margins, 146C; central parallel longitudinal stripes, 146B to 146D and 161D; venation, close to 145A.

Inflorescence description:

*Inflorescence form and arrangement*.—Long, open terminal panicles with tightly branched lateral panicles supported by erect and strong scapes; about 21 lateral panicles each with about 17 individual flowers; flowers distichous, sessile.

*Time to flower*.—Plants begin flowering about 12 to 14 weeks after planting.

*Inflorescence longevity*.—Inflorescences of the new Aechmca are very long-lasting, typically bract color will be maintained for about two months in the interior and about four months in the landscape depending on environmental conditions; inflorescences persistent.

*Fragrance*.—None detected.

*Inflorescence length*.—About 31.75 cm.

*Inflorescence width*.—About 28 cm.

*Flower buds*.—Length: About 2.2 cm. Diameter: About 8 mm. Shape: Ovoid, pointed. Texture: Smooth, glabrous. Color: Close to 162A.

*Flower length*.—About 2.1 cm.

*Flower diameter*.—About 5 mm.

*Petals*.—Quantity and arrangement: Three in a single whorl. Length: About 2.1 cm. Width: About 3 mm. Shape: Elongated ovate to lanceolate. Apex: Acute. Base: Truncate. Margin: Entire. Texture, inner and outer surfaces: Smooth, glabrous. Color: When opening and fully opened, inner surface: Close to 28B. When opening and fully opened, outer surface: Close to 28A.

*Sepals*.—Quantity and arrangement: Three in a single whorl. Length: About 2.7 cm. Width: About 8 mm. Shape: Elongated ovate to lanceolate. Apex: Acute. Base: Fused. Margin: Entire. Texture, inner and outer surfaces: Smooth, glabrous. Color: When opening and fully opened, inner surface: Close to 162B. When opening and fully opened, outer surface: Close to 163B to 163C.

*Primary bracts*.—Quantity and arrangement: One subtending each lateral panicle. Length: About 8.4 cm. Width: About 3 cm. Shape: Deltoid. Apex: Acuminate. Base: Truncate. Margin: Entire. Texture, inner and outer surfaces: Smooth, glabrous. Color, inner surface: Close to 179C. Color, outer surface: Close to 179B.

*Flower bracts*.—Quantity and arrangement: One per flower; subtending and closely appressed to the flower. Length: About 2.4 cm. Width: About 8mm. Shape: Narrowly deltoid. Apex: Acuminate. Base: Truncate. Margin: Entire. Texture, inner and outer surfaces: Smooth, glabrous. Color, inner and outer surfaces: Close to N167C.

*Scapes*.—Length, primary, to base of inflorescence: About 47 cm. Length, laterals: About 1.5 cm. Diameter, primary: About 6 mm. Diameter, laterals: About 4.5 mm. Strength, primary and laterals: Strong. Aspect, primary: Mostly upright. Aspect, laterals: Curving upright. Texture, primary and laterals: Smooth, glabrous. Color, primary and laterals: Close to 34B.

*Reproductive organs*.—Stamens: Quantity per flower: Six. Filament length: About 6 mm. Filament color: Close to 162A. Anther length: About 4 mm. Anther shape: Elongated oblong. Anther color: Close to 162C. Pollen: None observed, Pistils: Quantity per flower: One. Pistil length: About 1.3 cm. Style length: About 1 cm. Style color: Close to N163C. Stigma shape: Ovoid. Stigma color: Close to N163D. Ovary color: Close to 196D.

*Seeds*.—Seed production has not been observed on plants of the new *Aechmea*.

Temperature tolerance: Plants of the new *Aechmea* have been observed to tolerate temperatures ranging from about 3° C. to about 36° C.

Disease & pest resistance: Plants of the new *Aechmea* have been observed to be resistant to *Pythium* and *Phytophthora*. Plants of the new *Aechmea* not been observed to be resistant to pests and other pathogens common to *Aechmea* plants.

It is claimed:

1. A new and distinct *Aechmea* plant named 'Patricia's Secret' as illustrated and described.

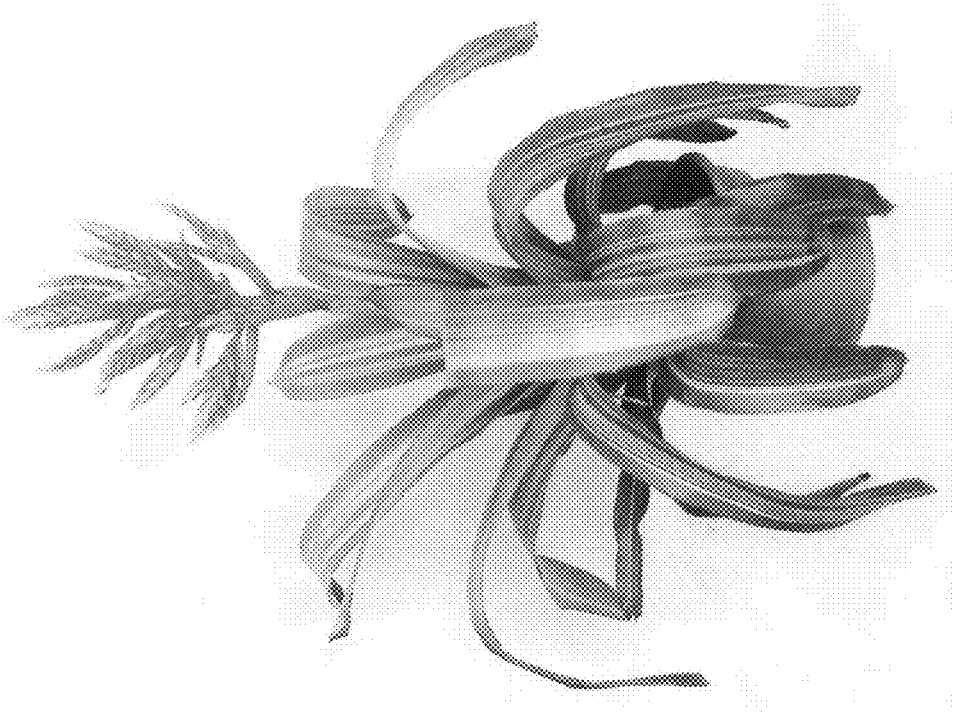
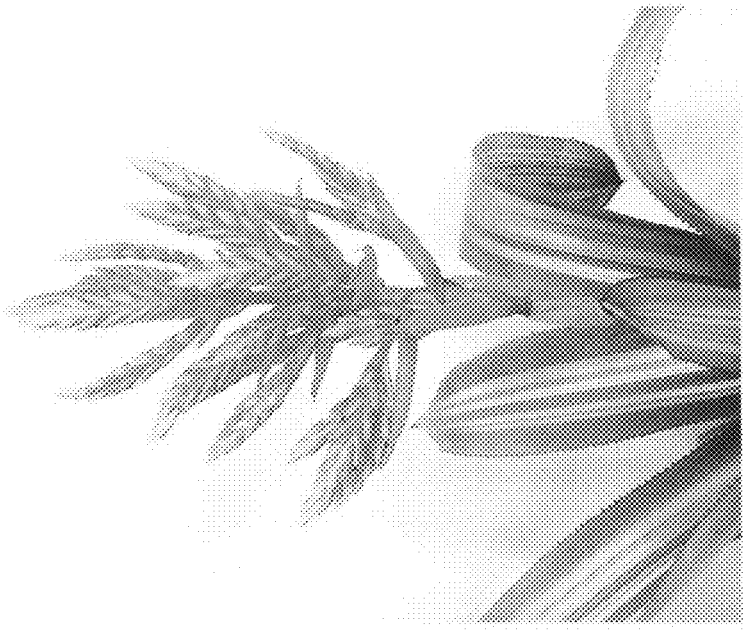

* * * * *